United States Patent
Hussain et al.

(10) Patent No.: US 8,217,207 B2
(45) Date of Patent: *Jul. 10, 2012

(54) PREPARATION AND PROVISION OF HIGH ASSAY DECABROMODIPHENYLETHANE

(75) Inventors: Saadat Hussain, Baton Rouge, LA (US); Arthur G. Mack, Prairieville, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/204,146

(22) Filed: Aug. 5, 2011

(65) Prior Publication Data

US 2011/0288225 A1  Nov. 24, 2011

Related U.S. Application Data

(62) Division of application No. 11/840,329, filed on Aug. 17, 2007, now Pat. No. 7,994,373.

(60) Provisional application No. 60/895,383, filed on Mar. 16, 2007.

(51) Int. Cl.
  C07C 25/00 (2006.01)
(52) U.S. Cl. ........................................ 570/184
(58) Field of Classification Search .................. None
  See application file for complete search history.

(56) References Cited

U.S. PATENT DOCUMENTS

| | | |
|---|---|---|
| 3,285,965 A | 11/1966 | Jenkner |
| 3,752,856 A | 8/1973 | Nagy et al. |
| 3,833,674 A | 9/1974 | Brackenridge |
| 3,965,197 A | 6/1976 | Stepniczka |
| 4,521,633 A | 6/1985 | Pedjac |
| 4,847,428 A | 7/1989 | Gu |
| 5,003,117 A | 3/1991 | Hussain |
| 5,008,477 A | 4/1991 | Hussain |
| 5,030,778 A | 7/1991 | Ransford |
| 5,055,235 A | 10/1991 | Brackenridge et al. |
| 5,077,334 A | 12/1991 | Hussain |
| 5,124,496 A | 6/1992 | Templeton et al. |
| 5,136,107 A | 8/1992 | Stephens et al. |

(Continued)

FOREIGN PATENT DOCUMENTS

CA  1321213 C  8/1993

(Continued)

OTHER PUBLICATIONS

"Chromatography, Liquid" in Kirk-Othmer Encyclopedia of Chemical Technology, John Wiley & Sons, Inc. pp. 440-468.*

(Continued)

*Primary Examiner* — Karl J Puttlitz
(74) *Attorney, Agent, or Firm* — Jeremy J. Kliebert

(57) ABSTRACT

High assay, reaction-derived decabromodiphenylethane product is prepared by feeding (i) diphenylethane or (ii) partially brominated diphenylethane having an average bromine number less than about two, or (iii) both of (i) and (ii), into the liquid confines of a reaction mixture. Such reaction mixture is (a) formed from components comprised of excess liquid bromine and aluminum-based Lewis acid bromination catalyst, and (b) maintained at one or more elevated reaction temperatures of from about 45°-90° C., and at least when elevated pressure is needed to keep a liquid state in the reaction mixture at the temperature(s) used, the reaction mixture is at such an elevated pressure, whereby ar-bromination occurs. The feeding is conducted at a rate slow enough to form high assay reaction-derived decabromodiphenylethane product, which is an effective flame retardant.

12 Claims, 3 Drawing Sheets

U.S. PATENT DOCUMENTS

| | | | |
|---|---|---|---|
| 5,302,768 | A | 4/1994 | Hussain |
| 5,324,874 | A | 6/1994 | Ransford et al. |
| 5,401,890 | A | 3/1995 | Parks |
| 5,457,248 | A | 10/1995 | Mack et al. |
| 5,741,949 | A | 4/1998 | Mack |
| 6,008,283 | A | 12/1999 | Rose et al. |
| 6,518,468 | B1 | 2/2003 | Parks et al. |
| 6,603,049 | B1 | 8/2003 | Parks et al. |
| 6,768,033 | B2 | 7/2004 | Parks et al. |
| 6,841,702 | B2 | 1/2005 | Magdolen et al. |
| 6,958,423 | B2 | 10/2005 | Parks et al. |
| 6,974,887 | B2 | 12/2005 | Parks et al. |
| 7,129,385 | B2 | 10/2006 | Dawson et al. |
| 7,408,088 | B1 * | 8/2008 | McKinnie ............ 570/206 |
| 7,851,662 | B2 | 12/2010 | McKinnie |
| 7,994,373 | B2 | 8/2011 | Hussain et al. |
| 2003/0144563 | A1 | 7/2003 | Falloon et al. |
| 2004/0110996 | A1 | 6/2004 | Parks et al. |
| 2005/0118080 | A1 | 6/2005 | Falloon et al. |
| 2005/0222473 | A1 | 10/2005 | Parks et al. |
| 2005/0234271 | A1 | 10/2005 | Parks et al. |
| 2007/0088184 | A1 | 4/2007 | Parks et al. |
| 2008/0194889 | A1 | 8/2008 | McKinnie |
| 2008/0227903 | A1 | 9/2008 | Hussain et al. |

FOREIGN PATENT DOCUMENTS

| | | |
|---|---|---|
| CA | 2094469 C | 2/1994 |
| CN | 1429800 A | 7/2003 |
| DE | 2950877 A1 | 6/1981 |
| DE | 3326343 A1 | 1/1985 |
| DE | 3422673 A1 | 12/1985 |
| DT | 2400455 | 2/1975 |
| EP | 0107978 A1 | 5/1984 |
| EP | 0265150 B1 | 4/1988 |
| EP | 0347116 A2 | 12/1989 |
| EP | 0445595 A2 | 9/1991 |
| EP | 0571859 A2 | 12/1993 |
| GB | 981833 | 1/1965 |
| GB | 1278603 | 6/1972 |
| GB | 1411524 | 10/1975 |
| GB | 2143521 | 2/1985 |
| JP | 50-018430 | 2/1975 |
| JP | 52-039639 | 3/1977 |
| JP | 52-139033 | 11/1977 |
| JP | 53-053629 | 5/1978 |
| JP | 53-116332 | 10/1978 |
| JP | 54-044623 | 4/1979 |
| JP | 58-222043 | 12/1983 |
| JP | 62-004241 | 1/1987 |
| JP | 10-158202 | 6/1998 |
| JP | 10-175893 | 6/1998 |
| WO | 93/24434 A1 | 12/1993 |
| WO | 94/22978 A1 | 10/1994 |
| WO | 03/055832 A1 | 7/2003 |

OTHER PUBLICATIONS

Albemarle Corporation, Saytex 8010 Flame Retardant, XP-002458574, 2001, 2-pages.

Yang, Ze-hui, et al., "Technological Progress in Catalytic Synthesis of Decabromodiphenyl Ether by Brominating Diphenyl Oxide with Bromine Chloride", Fine Chemicals, vol. 19, No. 1, Jan. 2002, pp. 42-44, abstract only translated.

Knoppen, R., et al., "Decabromodiphenylethane", Acta Cryst., 2007, E63, pp. o585-o586.

* cited by examiner

PREPARATION AND PROVISION OF HIGH ASSAY DECABROMODIPHENYLETHANE

REFERENCE TO RELATED APPLICATIONS

This application is a division of U.S. application Ser. No. 11/840,329, filed Aug. 17, 2007, now allowed, which in turn claims the benefit and priority of U.S. Provisional Application No. 60/895,383, filed Mar. 16, 2007, the disclosure of which is incorporated herein by reference.

TECHNICAL FIELD

This invention relates to the preparation and provision of high assay reaction-derived decabromodiphenylethane products and their use.

BACKGROUND

Decabromodiphenylethane is a time-proven flame retardant for use in many flammable macromolecular materials, e.g. thermoplastics, thermosets, cellulosic materials and back coating applications of very high quality.

Governmental regulating agencies tend to be moving away from partially brominated analogs and more towards perbrominated compounds as evidenced by the recent EU RoHS (Restriction on Hazardous Substances) directive (2002/95/EC) relating in part to partially brominated diphenyl oxides. Even with the exemption of decabromodiphenyl oxide from RoHS per 2005/717/EC, the regulations have not been clear enough in terms of the acceptable nonabromodiphenyl oxide content in electrical and electronic products. Some end users therefore find it uncomfortable using the commercial decabromodiphenyl oxide in which significant amounts of nonabromodiphenyl oxide exists as impurity. In order to meet the strictest interpretation of RoHS by the end users, a high assay version of decabromodiphenyl oxide is being marketed by Albemarle Corporation. In view of the confusion concerning the presence of small quantities of lower brominated impurities in the flame retardant products, there is thus a need in the marketplace for very high assay perbrominated flame retardants.

Decabromodiphenylethane is presently sold as a powder derived from the bromination of 1,2-diphenylethane. Among prior processes for effecting such bromination are the bromination processes described in U.S. Pat. Nos. 6,518,468; 6,958,423; 6,603,049; 6,768,033; and 6,974,887. Decabromodiphenylethane has been commercially produced by the assignee of this application for many years using a standard process. Each batch of product was analyzed by a GC procedure. A review of the GC analyses indicated that the average bromine content of over 4000 batches of decabromodiphenylethane product was 97.57 area percent with a 3-sigma precision of ±1.4 area percent. The equipment used for those analyses did not include a present-day data collection system that can electronically fine tune the peaks of the chromatogram. In some cases, the analysis of the product from a given run provided assays of decabromodiphenylethane in the region of about 99 area percent and above, and in some other cases significantly lower GC assays were obtained. The reasons for this variance cannot be established from the information available.

Gas chromatographic analysis of commercial decabromodiphenylethane products available in the marketplace from other manufacturers have, in some cases, also given assays of a decabromodiphenylethane product as high as about 99.6 area percent. In other cases, GC analyses of commercial decabromodiphenylethane products available in the marketplace have indicated the presence of much lower amounts of decabromodiphenylethane in the product. Information on the method by which such high assay products were produced and the purification procedures used, if any, is not generally available to the public.

From at least the standpoint of providing environmentally-friendly process technology, it would be highly desirable if commercially feasible processes could be found that would produce on a consistent basis a decabromodiphenylethane product that comprises at least about 99.50 GC area percent of decabromodiphenylethane ($Br_{10}DPE$), with the balance consisting essentially of nonabromodiphenylethane ($Br_9DPEi$). Such product is hereinafter often referred to in the specification and claims hereof as "high assay decabromodiphenylethane product". Moreover, this high assay decabromodiphenylethane product is a "reaction-derived" product which term as used herein including the claims, means that the composition of the product is reaction determined and not the result of use of downstream purification techniques, such as recrystallization or chromatography, or like procedures that can affect the chemical composition of the product. Adding water or an aqueous base such as sodium hydroxide to the reaction mixture to inactivate the catalyst, and washing away of non-chemically bound impurities by use of aqueous washes such as with water or dilute aqueous bases are not excluded by the term "reaction-derived". In other words, the products are directly produced in the synthesis process without use of any subsequent procedure to remove or that removes nonabromodiphenylethane from decabromodiphenylethane.

BRIEF SUMMARY OF THE INVENTION

A process has now been found that can produce high assay reaction-derived decabromodiphenylethane product comprising at least about 99.50 GC area percent of decabromodiphenylethane ($Br_{10}DPE$), and having a nonabromodiphenylethane ($Br_9DPE$) content of about 0.50 GC area percent or less, preferably about 0.30% or less, and more preferably, about 0.10% or less, these GC analytical criteria being obtained using present-day analytical instrumentation that electronically fine tunes the peaks of the chromatogram. Indeed, it has been found possible, pursuant to this invention, to produce a decabromodiphenylethane product having an assay of at least about 99.80 GC area percent of decabromodiphenylethane ($Br_{10}DPE$) with the balance of the assay consisting essentially of nonabromodiphenylethane ($Br_9DPE$). Moreover, the processes of this invention for achieving such high assay reaction-derived decabromodiphenylethane product are deemed capable of producing such decabromodiphenylethane products on a consistent basis.

Another feature of this invention is that, as far as is known, it has not been known heretofore how to prepare on a consistent basis a high assay reaction-derived decabromodiphenylethane product meeting the above criteria. Only in a few instances have analyses of prior plant runs yielded GC values above 99.50 GC area percent of decabromodiphenylethane ($Br_{10}DPE$) and these analytical results were obtained using equipment which did not have a present-day data collection system that could fine tune the peaks of the chromatogram, and based on the averaged results of over 4000 such runs, it is reasonable to conclude that those few instances were artifacts. And in any event, even if the GC results were valid within modern-day capabilities of precision, the precise experimental conditions that could be said to have been responsible for achieving such results are unknown. Moreover, even using the older GC data collection system with its relatively low averaged values with the precision at 3-sigma, no analysis report referred to above yielded a decabromodiphenylethane ($Br_{10}DPE$) value as high as 99.80 area percent.

Therefore, consistent with the desire for higher assay flame retardants for environmentally friendly reasons, this invention provides in one of its embodiments a process for producing high assay reaction-derived decabromodiphenylethane product. This process comprises feeding (i) diphenylethane or (ii) partially brominated diphenylethane having an average bromine number less than about two, or (iii) both of (i) and (ii), into the liquid confines of a reaction mixture, which reaction mixture is:

a) formed from components comprised of excess liquid bromine and aluminum-based Lewis acid bromination catalyst, and into which at least (i), (ii), or (iii) is fed, and b) maintained at one, or at more than one, elevated reaction temperature in the range of about 45° C. up to about 65° C., and at least when elevated pressure is needed in order to keep a liquid state in the reaction mixture at the temperature(s) used, the reaction mixture is at elevated pressure sufficient to keep a liquid state in the reaction mixture at the temperature(s) used, so that ar-bromination occurs, the feeding being conducted at a rate slow enough to form high assay reaction-derived decabromodiphenylethane product. This embodiment is based on experiments which have demonstrated that the slower the feed, the higher the assay. Progress of the reaction and assay of decabromodiphenylethane product can be followed analytically by use of a GC procedure such as described hereinafter.

The fact that in the foregoing process a slow feed rate is employed is deemed counter-intuitive. In the process, high assay reaction-derived decabromodiphenylethane product is formed as solid particles in the hot liquid bromine medium. Decabromodiphenylethane is very insoluble in bromine and common bromination reaction solvents such as methylene bromide. Since the solid particles are forming in the liquid medium more slowly during a prolonged feeding period, coproducts formed in the reaction could be expected to become entrapped within these particles. Once formed, the vast majority of these particles would be expected to remain unchanged because of their poor solubility in the reaction solvent. Thus to avoid such a situation it would seem desirable to feed the diphenylethane rapidly in order to achieve rapid bromination and formation of the decabromodiphenylethane product before precipitation starts, or at least after as little precipitation formation as possible.

Processes of the above embodiment are well suited for use in relatively small plant operations where large volumes of product are not required. However, because of the use of a slow feed which prolongs the reaction time for a given quantity of diphenylethane and/or partially brominated diphenylethane having an average bromine number of less than about two, the throughput or productivity of a larger scale process operation is lower than desired. In other words, from a manufacturing perspective, slow feed rates required for higher assay product significantly reduce plant throughput by reducing the number of batches made. To overcome this situation, this invention provides in preferred embodiments processes which use suitably slow feed rates but which at the same time can significantly increase plant throughput and productivity of high assay reaction-derived decabromodiphenylethane product. This is accomplished by use of two or more feeding devices such as dip tubes, jet injectors, subsurface feeding ports, or the like.

Thus, in accordance with this invention, there is provided as a preferred embodiment, a process of producing high assay reaction-derived decabromodiphenylethane product. This process comprises feeding (i) diphenylethane (DPE) or (ii) partially brominated diphenylethane having an average bromine number less than about two, or (iii) both of (i) and (ii), into the liquid confines of a reaction mixture, which reaction mixture is:

a) formed from components comprised of excess liquid bromine and aluminum-based Lewis acid bromination catalyst, and into which at least (i), (ii), or (iii) is fed, and b) maintained at one, or at more than one, elevated reaction temperature in the range of about 45° C. up to about 65° C., and at least when elevated pressure is needed in order to keep a liquid state in the reaction mixture at the temperature(s) used, the reaction mixture is at elevated pressure sufficient to keep a liquid state in the reaction mixture at the temperature(s) used, so that ar-bromination occurs; and c) wherein the feeding is conducted at a rate slow enough to form high assay reaction-derived decabromodiphenylethane product; and d) wherein the feeding is in the form of two or more individual spaced-apart feeds into the confines of the reaction mixture from jets or orifices disposed in one or more feeding devices or dip tubes such that each of the resulting two or more individual flows of DPE and/or partially brominated DPE having an average bromine number less than about 2 emanating or issuing from these jets or orifices into the reaction mixture comes into contact with excess bromine and aluminum-based catalyst in a portion of the overall reaction mixture which is sufficiently separate or isolated from the other individual flow or flows of DPE and/or partially brominated DPE having an average bromine number less than about 2 from the one or more other jets or orifices so that two or more individual spaced-apart localized reaction zones are created and maintained within the confines of the reaction mixture at least for a time sufficient to ensure bromination to achieve the desired assay.

It can thus be seen that in this preferred embodiment:

1) the spacing between or among the two or more individual streams or flows of DPE and/or partially brominated DPE having an average bromine number less than about 2 emanating from the feed jets or orifices is large enough;

2) the overall reaction mixture is kept under conditions that avoid overlapping of the respective feeds and flows from the two or more streams or flows of DPE and/or partially brominated DPE having an average bromine number less than about 2 emanating from the feed jets or orifices so that each such stream or flow continues to mix with a portion of the bromine and aluminum-based catalyst to form a separate individual reaction zone within the confines of the reaction mixture; and 3) the reactions taking place in the resultant separate individual reaction zones within the confines of the overall reaction mixture result in the formation of high assay reaction-derived decabromodiphenylethane product before such reaction product co-mingles with reaction product from any other individual reaction zone within the confines of the overall reaction mixture;

whereby high assay reaction-derived decabromodiphenylethane product is concurrently and progressively formed in two or more separate reaction zones created and maintained within the confines of the reaction mixture by virtue of the disposition of the respective feeds of DPE and/or partially brominated DPE having an average bromine number less than about 2 into the overall reaction mixture, and the appropriately-slow rates at which such respective feeds enter into the overall reaction mixture. Such appropriately-slow rates of the two or more feeds into the confines of the reaction mixture ensure that the reactants have time enough to react to form high assay reaction-derived decabromodiphenylethane product in the respective separate localized reaction zones within the confines of the reaction mixture before such products merge together within the body of the overall reaction mixture.

A further embodiment of this invention is a reaction-derived decabromodiphenylethane product comprising (i) at least about 99.50 GC area % of decabromodiphenylethane and (ii) nonabromodiphenyl ethane in an amount not exceeding about 0.50 GC area %. In a preferred embodiment, such reaction-derived decabromodiphenylethane product comprises (i) at least about 99.80 GC area percent of decabromodiphenylethane and (ii) nonabromodiphenyl ethane in an amount not exceeding about 0.20 GC area %. A particularly preferred embodiment is reaction-derived decabromodiphenylethane product comprising (i) at least about 99.90 GC area % of decabromodiphenylethane and (ii) nonabromodiphenyl ethane in an amount not exceeding about 0.10 GC area %. All such percentages as used herein, including the claims, are GC area percentages using the present-day GC analytical procedure described hereinafter.

Still other embodiments of this invention relate to flame retarded compositions in which high assay reaction-derived decabromodiphenylethane product is employed as a flame retardant, to processes for forming such compositions and to methods of converting such compositions into flame retarded finished end products.

The above and other embodiments of this invention will be still further apparent from the ensuing description and appended claims.

FURTHER DETAILED DESCRIPTION OF EMBODIMENTS OF THIS INVENTION

Figure 1:
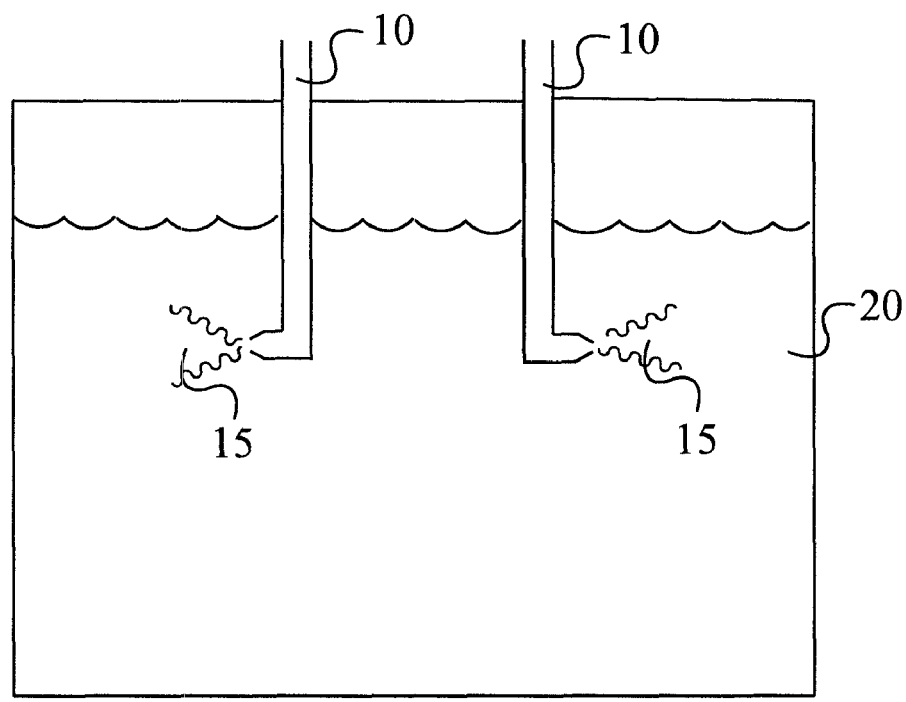
FIG. 1 illustrates schematically in side view a reaction vessel equipped pursuant to a preferred embodiment of this invention with, in this case, two subsurface feeding devices and non-overlapping undiluted flows issuing from the two feeding devices within the confines of the reaction mixture.

In one of the embodiments of this invention, high assay reaction-derived decabromodiphenylethane product is produced by feeding (i) diphenylethane (DPE) or (ii) partially brominated diphenylethane having an average bromine number less than about two, or (iii) both of (i) and (ii), into the liquid confines of a reaction mixture, which reaction mixture is:

a) formed from components comprised of excess liquid bromine and aluminum-based Lewis acid bromination catalyst, and into which at least (i), (ii), or (iii) is fed, and b) maintained at one, or at more than one, elevated reaction temperature in the range of about 45° C. up to the boiling temperature of the reaction mixture, and preferably in the range of about 55° C. up to the boiling temperature of the reaction mixture, which reaction mixture can be under superatmospheric pressure so that the boiling temperature used is above the normal atmospheric boiling temperature of any component in the reaction mixture, so that ar-bromination occurs, the feeding being conducted at a rate slow enough to form high assay reaction-derived decabromodiphenylethane product. Experimental work has demonstrated that for a given quantity of DPE and/or partially brominated DPE having an average bromine number less than about 2, the slower the rate of feed to the reaction mixture containing an excess of bromine and aluminum-based catalyst, the higher the assay of the decabromodiphenylethane product formed. While various ancillary factors can affect the rate to be used in order to achieve production of high assay reaction-derived decabromodiphenylethane product (e.g., reaction scale, reaction temperature, etc.), generally speaking at a one liter reaction scale and at a reaction temperature of 60° C., a feed rate of no more than about 0.5 grams per minute through each dip tube serves as a good reference point for assessing a suitable feed rate at a larger scale of operation under comparable temperature conditions. Thus, if the rate of feed has not been established for any given proposed operation, a few pilot experiments utilizing the above reference point should enable preparation of high assay reaction-derived decabromodiphenylethane product at a different scale of operation. This embodiment is based on experiments conducted on a 0.5 liter scale at about 60° C. which have demonstrated that the slower the feed, the higher the assay. As noted above, progress of the reaction and assay of decabromodiphenylethane product can be followed analytically by use of a GC procedure such as described hereinafter.

In preferred embodiments of this invention, sometimes referred to hereinafter as multi-feed embodiments, use is made of two or more feeds of i) diphenylethane or (ii) partially brominated diphenylethane having an average bromine number less than about two, or (iii) both of (i) and (ii) into the liquid confines of a reaction mixture. As used herein, including the claims, the term "liquid confines" denotes that the feed occurs below the surface of the liquid of the reaction mixture and is directly or indirectly (e.g., by bouncing off of a baffle plate or reactor wall) fed into a portion of the body of the continuous liquid phase of the reaction mixture.

One of the features of the preferred multi-feed embodiments of this invention is that the each of the two or more feeds of diphenylethane and/or partially brominated diphenylethane is conducted at a slow enough rate to enable the flow of DPE or partially brominated DPE having an average bromine number less than about 2 to react in a portion of the reaction mixture with bromine in the presence of an aluminum-based catalyst so that high assay reaction-derived decabromodiphenylethane product is produced by the reaction before the product comes into contact with the flow emanating from another feed within the confines of the reaction mixture. In short, the feeding devices should be installed in the reactor in such a way so as not to allow the respective feeds to mix together before complete bromination has taken place. The term "complete bromination" as used herein including the claims does not necessarily imply 100% bromination to $Br_{10}DPE$ even though this is not excluded from the term. Thus, if the desired assay of the product is, say, 99.50 GC area percent, then complete bromination in such case can mean 99.50 GC area percent.

Another of the features of the multi-feed embodiments of this invention is the maintenance of a reaction mixture under conditions that balance the rate of the feeds of DPE and/or partially brominated DPE having an average bromine number less than about 2, each of which enters into a separate, spaced-apart, localized reaction zone within the reaction mixture such that the contents of the localized reaction zones within the reaction mixture are not swept into each other prior to formation of high assay reaction-derived decabromodiphenylethane product within each successive portion of each such continuously formed reaction zone.

Generally speaking, the farther apart are the flows emanating from the respective feeding devices, the greater can be the amount of fluid motion, stirring, agitation, or shaking within the reaction mixture. Each such flow should create and maintain a localized reaction zone separate and apart from each other localized reaction zone within the confines of the liquid phase of the reaction mixture.

In the multi-feed embodiments of this invention, the flows of two or more separate feeds into and within the confines of the liquid phase of the reaction mixture are directed so that they do not intersect or overlap each other prior to the generally localized bromination reactions taking place in the different respective separate portions of the reaction mixture into which the respective feeds proceed. Such controlled feeds and flows are illustrated schematically, for example, in FIGS. 1, 2, and 3.

Another way of preventing overlap of the flows emanating from each of a plurality of subsurface feeding devices is to provide and maintain screens or baffle plates within the reaction zone which serve to segregate from each other the undiluted feeds emanating from the respective feeding devices such that no undiluted flow from any such device directly impinges upon an undiluted flow from any other such device. Thus, in this case, each feeding device is separated from each other feeding device by such a screen or baffle plate. Such arrangements of feeding devices and screens or baffle plates are illustrated schematically in FIGS. 4 and 5.

In conducting the processes of this invention the reaction mixture is maintained at one or more reaction temperatures in the range of about 45° C. to about 90° C. and the reaction mixture is at elevated pressure sufficient to keep bromine and, if used, organic solvent or diluent, in the liquid state at the temperature(s) used, at least when elevated pressure is needed in order to keep bromine and, if used, such solvent or diluent in the liquid state at the temperature(s) used. Preferably, the reaction is performed at one or more temperatures in the range of about 55° C. to about 65° C. using superatmospheric pressure where necessary.

Increased reaction pressure tends to increase the extent of bromination. Nevertheless, pursuant to this invention, it is possible to operate at atmospheric, subatmospheric and/or at superatmospheric pressures in the range of about 1 to about 50 psig (ca. $1.08 \times 10^5$ to $4.46 \times 10^5$ Pa). However, the pressure is preferably no more than autogenous pressure in a closed reaction system.

As used herein, including the claims, the term "diphenylethane" means 1,2-diphenylethane unless otherwise noted. 1,2-Diphenylethane is also known as dibenzyl or bibenzyl.

The feeds used in the practice of this invention are composed of (i) diphenylethane or (ii) partially brominated diphenylethane having an average bromine number of less than about two, or (iii) both of (i) and (ii). Bromine number is the average number of ring-substituted bromine atoms per molecule of diphenylethane. When diphenylethane and partially brominated diphenylethane are used as feeds, these feed components can be fed as a preformed mixture or they can be fed separately, either concurrently, or sequentially. The components in such mixtures or separate feeds can be in any proportions relative to each other.

Excess bromine is used in the Lewis acid catalyzed bromination reaction. Typically, the reaction mixture will contain in the range of at least about 14 moles of bromine per mole of diphenylethane and/or partially brominated diphenylethane to be fed thereto, and preferably, the reaction mixture contains in the range of about 16 to about 25 moles of bromine per mole of diphenylethane and/or partially brominated diphenylethane to be fed thereto. It is possible to use more than 25 moles bromine per mole of diphenylethane but ordinarily this is unnecessary.

Aluminum-based Lewis acid bromination catalysts are used in the practice of this invention. The catalyst component as charged to the reaction mixture can be in the form of metallic aluminum such as in the form of aluminum foil, aluminum turnings, aluminum flakes, aluminum powder, or other subdivided forms of aluminum metal. Alternatively, the catalyst component as charged to the reaction mixture can be in the form of an aluminum halide in which the halogen atoms are chlorine atoms, bromine atoms, or a combination of chlorine atoms and bromine atoms. A feed of aluminum chloride is desirable from the standpoints of economics and ready availability of that material. A feed of aluminum bromide is desirable from the standpoint that it is more soluble in liquid bromine than aluminum chloride and thus can be fed into the reaction zone along with liquid bromine, which is a desirable way to operate. The amount of aluminum-based catalyst used should be sufficient to initiate and maintain the desired bromination reaction. Generally speaking, the amounts of aluminum catalyst used should provide an aluminum:bromine mole ratio in the range of about 0.0054:1 to about 0.014:1 and preferably in the range of about 0.005:1 to about 0.008:1.

The reaction mixture should of course be kept anhydrous and free from exposure to light. If desired, a suitable inert organic solvent such as a halogenated hydrocarbon (e.g., bromochloromethane, dibromomethane, 1,2-dibromoethane, 1,2-dichloroethane, 1,1-dibromoethane, tribromomethane, or the like) can be used. However, use of a liquid bromine as the liquid phase component of the reaction mixture is preferred.

The bromination can be conducted on a batch, semi-continuous, or continuous basis. Conduct of the reaction on a batch basis is simpler as it typically enables use of slower feeds and longer reaction times than other modes of operation.

Pursuant to this invention, bromination is carried out during a period of time or average residence time long enough and with the feed rate being at a rate slow enough to form a high assay reaction-derived decabromodiphenylethane product. The particular period of time or average residence time used for the bromination is dependent upon a number of factors such as the scale of operation, the temperature at which the reaction is being conducted, the rate at which the diphenylethane and/or partially brominated diphenylethane is being fed into the reaction mixture, the concentration of the aluminum-based catalyst present in the reaction mixture, the amount of the motion to which the liquid phase of the reaction mixture is undergoing during the feed, and so on. Thus, no universal set of feed rates and reaction times exists as the operating conditions can have a significant effect on the variables of feed rate and reaction times. In any situation where a suitable or optimum feed rate and reaction time have not been established, a few pilot experiments at a suitable larger scale of operation should be sufficient to enable realization of the benefits of the practice of this invention. In general, larger scale batch-type operations should be conducted with somewhat longer feed and total bromination reaction times than those given in this paragraph.

The coproduct in the reaction, hydrogen bromide, is typically released in part in the form of a vapor. For reasons of economy of operation it is desirable to recover the coproduct hydrogen bromide such as by passing the vapors into a scrubbing system in which the hydrogen bromide is converted either to hydrobromic acid using water as the scrubbing liquid, or into a hydrobromic acid salt using an aqueous solution of metal base such as aqueous sodium hydroxide as the scrubbing liquid.

Upon completion of the bromination reaction, it is desirable to inactivate the catalyst by use of an aqueous medium such as water or an aqueous solution of a water-soluble inorganic base such as sodium hydroxide or potassium hydroxide. The solid product is then recovered from the liquid phase by filtration, centrifugation, decantation, or other physical separation procedure.

The separated product is typically washed with water or dilute aqueous bases in order to wash away non-chemically bound impurities. The product can then be subjected to finishing operations such as heating to remove free bromine and grinding to convert the product to a uniform particle size before packaging.

In order to determine the composition of the brominated product formed in a process of this invention, a gas chromatographic procedure is used. The gas chromatography is conducted on a Hewlett-Packard 5890 Series II gas chromatograph (or equivalent) equipped with a flame ionization detector, a cool on-column temperature and pressure programmable inlet, and temperature programming capability. The column is a 12QC5 HTS capillary column, 12 meter, 0.15μ film thickness, 0.53 mm diameter, available from SGE, Inc., part number 054657. Conditions are: detector temperature 350° C.; inlet temperature 70° C.; heating at 125° C./min to 350° C. and holding at 350° C. until the end of the run; helium carrier gas at 10 ml/min.; inlet pressure 4.0 psig (ca. $1.29 \times 10^5$ Pa), increasing at 0.25 psi/min. to 9.0 psig (ca. $1.63 \times 10^5$ Pa) and holding at 9.0 psig until the end of the run; oven temperature 60° C. with heating at 12° C./min. to 350° C. and holding for 10 min.; and injection mode of cool on-column. Samples are prepared by dissolving, with warming, 0.003 grams in 10 grams of dibromomethane and injection of 2 microliters of this solution. The integration of the peaks is carried out using Target Chromatography Analysis Software from Thru-Put Systems, Inc. However, other and commercially available software suitable for use in integrating the peaks of a chromatograph may be used. Thru-Put Systems, Inc. is currently owned by Thermo Lab Systems, whose address is 5750 Major Blvd., Suite 200, Orlando, Fla. 32819. The address of SGE, Incorporated is 2007 Kramer Lane, Austin, Tex. 78758.

Figure 2:
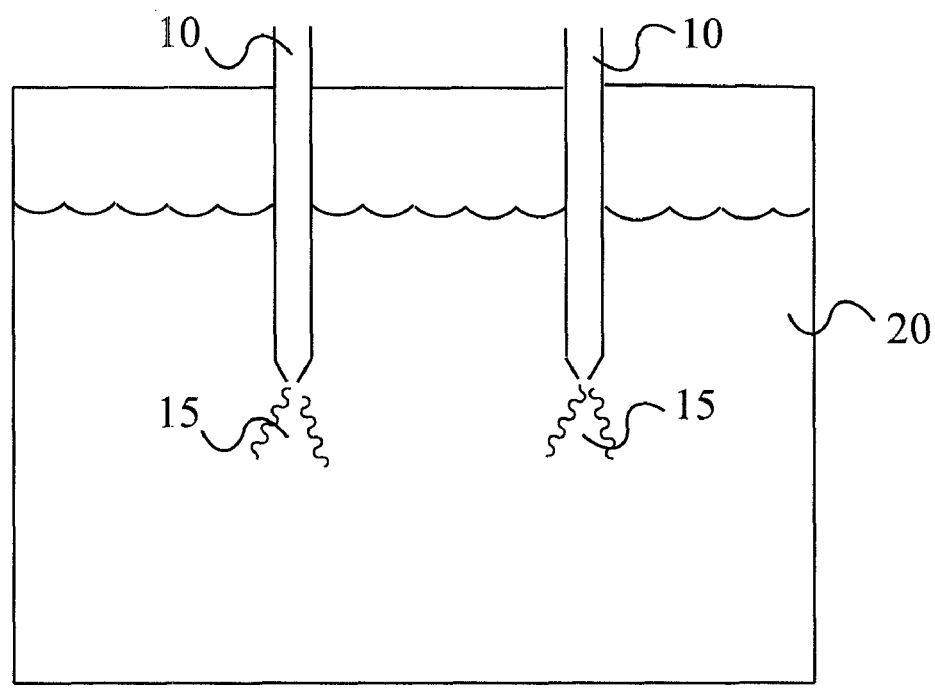
FIG. 2 illustrates schematically in side view a reaction vessel equipped generally as in FIG. 1 except that the non-overlapping undiluted flows issuing from the two feeding devices are directed downwardly rather than laterally.

Referring now to the drawings, FIGS. 1 and 2 illustrate use of at least two separate feeding devices 10,10 which feed DPE and/or partially brominated DPE having an average bromine number less than about 2 within the confines of the reaction mixture 20. In FIG. 1 the flows 15,15 emanating from the respective orifices or nozzles of the feeding devices are caused to flow into the reaction mixture in opposite directions from each other. In FIG. 2 the flows 15,15 are both directed downwardly, illustrating the fact that the flows can be caused to flow in any suitable directions within the body of the reaction mixture, so long as they do not intersect or otherwise come in contact with each other. It will of course be appreciated that the flows 15,15 as illustrated do not define or circumscribe the shape or size of the flows issuing from the orifices or nozzles.

Figure 3:
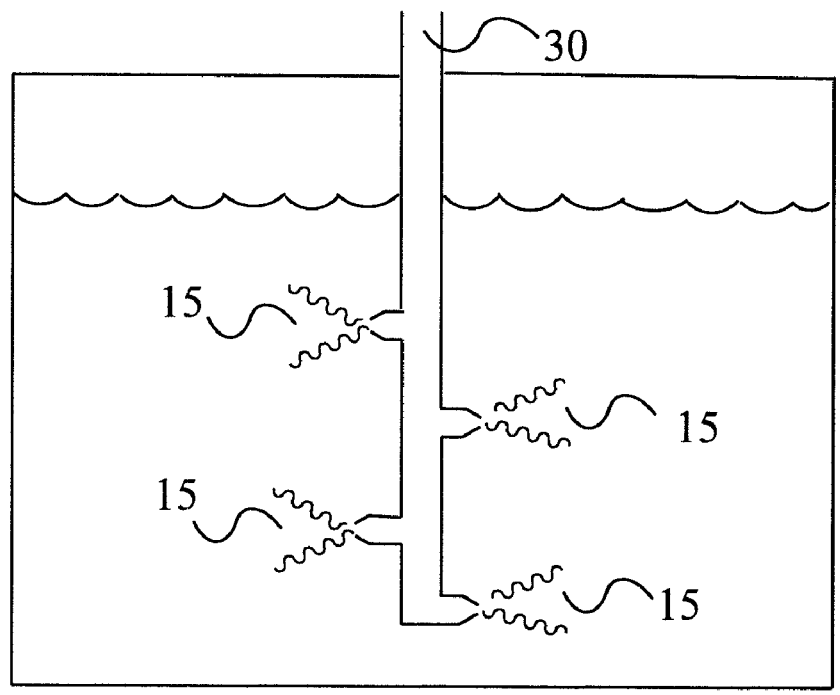
FIG. 3 illustrates schematically in side view a reaction vessel equipped pursuant to a preferred embodiment of this invention with, in this case, one subsurface feeding device provided with a plurality of oppositely disposed feeding nozzles at different elevations along the main conduit of the device so that a plurality of spaced-apart feeds enter into the confines of the reaction mixture.

FIG. 3 illustrates the use of a single feeding device 30 equipped with multiple nozzles or feed ports. It will again be seen that the respective flows 15,15,15,15 from the nozzles or feed ports proceed in directions that do not overlap each other.

Figure 4:
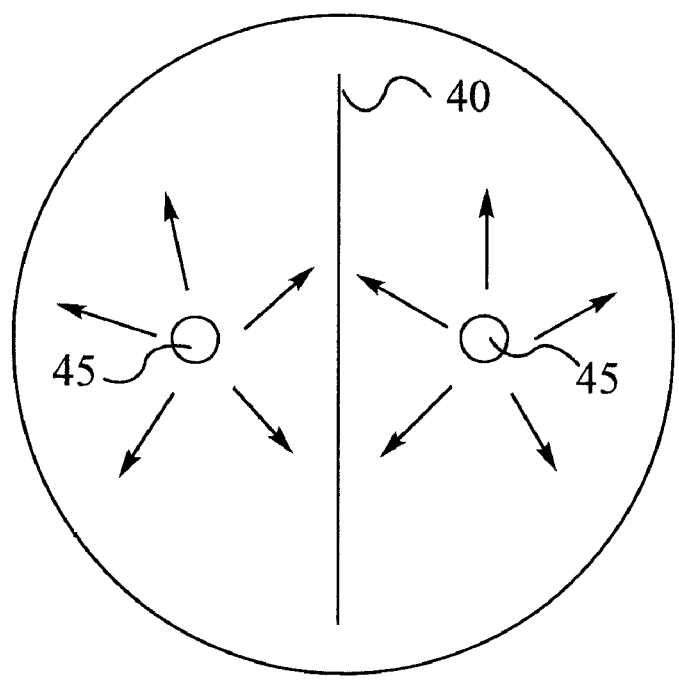
FIG. 4 illustrates schematically in top view a reaction vessel equipped pursuant to a preferred embodiment of this invention with, in this case, two feeding devices each with a plurality of laterally directed non-overlapping subsurface flows issuing therefrom (represented by arrows) and wherein a baffle plate or screen is interposed between these two feeding devices.
Figure 5:
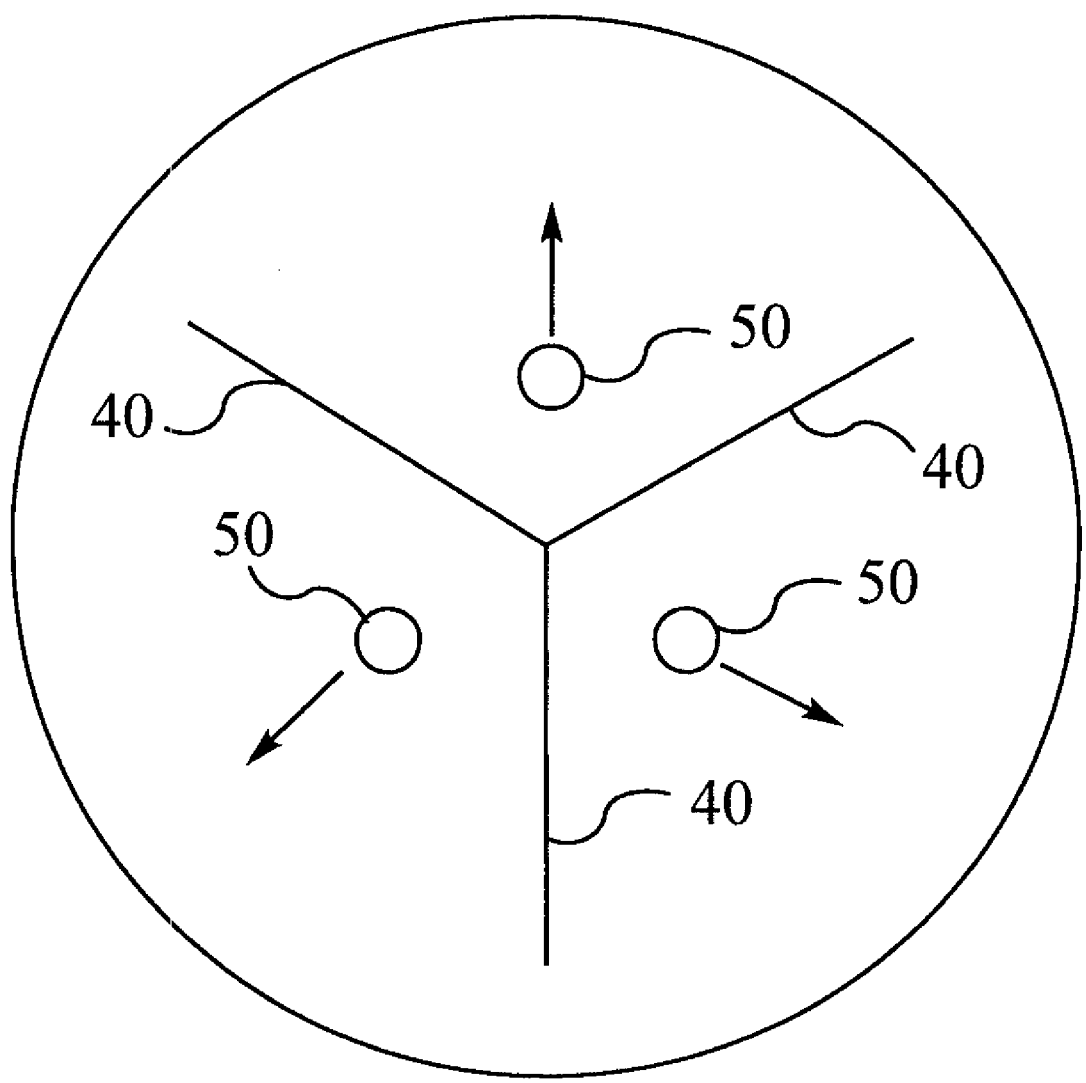
FIG. 5 illustrates schematically in top view a reaction vessel equipped pursuant to a preferred embodiment of this invention with, in this case, three feeding devices each having a single feed nozzle or orifice and a non-overlapping subsurface flow issuing therefrom (represented by arrows), these non-overlapping flows being separated from each other by a baffle plate or screen interposed between each other.

FIGS. 4 and 5 illustrate in schematic top view the use of one or more baffle plates or screens to assist in maintaining separate individual reaction zones within the body of the reaction mixture. In FIG. 4, one baffle plate or screen 40 is disposed between feeding devices 45,45. The system schematically illustrated in FIG. 4 also includes two vertically disposed feeding devices such as vertical conduits or tubes closed at their bottom end and having ports or nozzles around their circumference. As shown by the arrows in FIG. 4, the flows from the ports or nozzles travel in outward angularly disposed directions around the circumference of the conduits or tubes. In the particular case illustrated in FIG. 4, five flows radially emanate from each conduit or tube so that they do not intersect each other. In the system schematically depicted in FIG. 4, the five ports or nozzles on each feeding device can be at the same or different elevation so that the respective flows emanating from each conduit are either at the same elevation or at different elevations relative to each other. In FIG. 5, three vertically disposed feeding devices 50,50,50 such as vertical conduits or tubes closed at their bottom end and having ports or nozzles around their circumference are illustrated. Each of these feeding devices is separated from its two adjacent feeding devices by a baffle plate or screen 40 which are connected together at their inner ends. In FIG. 5, the single arrows emanating from each conduit or tube 50 illustrate the use of a single flow emanating from each such feeding device.

The following examples are presented for purposes of illustration. These examples are not intended to limit the invention to only the particular operations and conditions used therein. Examples 1 and 3 illustrate the benefits pursuant to this invention of using feed rates that are slow enough to enable the preparation of high assay reaction-derived decabromodiphenylethane product. Examples 2 and 4 are examples of preferred embodiments of this invention in which two suitably spaced-apart dip tubes using the same relatively slow feed rate were used. The flows from these two dip tubes did not intersect or mix together prior to complete bromination.

EXAMPLE 1

A 500 mL four-necked round bottom flask was equipped with a mechanical stirrer, a thermometer with a temperature regulator, a 1/16-inch ID Teflon polymer dip tube, a reflux condenser which was connected to an ice-cold caustic scrubber and a heating mantle. The flask was charged with bromine (129 mL) and anhydrous aluminum chloride (1.82 g). The contents were stirred and heated to 55° C. A solution of diphenylethane (18.2 g, 0.1 mole) in dibromomethane (18 mL, 29 wt % DPE solution) prepared earlier, was then fed to the reactor containing bromine and catalyst, sub-surface via the dip tube using a peristaltic pump, at 55° C., over a period of 6.5 hours. The reaction mixture was then stirred at reflux (65° C.) for an additional one hour. The contents were cooled to room temperature. Water (250 mL) was now added to the mix. A Barret trap was installed between the reactor and the reflux condenser and the reaction mixture was heated to remove excess bromine and solvent, while continuously recycling the water back to the reactor. The excess bromine/dibromomethane was removed via steam distillation until the vapor temperature reached a temperature of 100° C. The product separated as a solid powder in water. This slurry was cooled to room temperature and then caustic solution (50% aqueous sodium hydroxide, 22 g) was added. The slurry was filtered and the filter cake was washed with water (3×150 mL). The solid was removed in a dish and was allowed to dry in air overnight. This gave a solid powder weighing 102.1 g. A small sample was submitted for GC analysis which showed the composition to be 99.95 area % decabromodiphenylethane and 0.05 area % of unidentified components which were assumed to be Br-9 derivative.

EXAMPLE 2

This reaction was an exact repeat of Example 1 except that two dip tubes were employed to feed the DPE solution and the feed rate was the same through each dip tube. The feed was over in 3.08 hours. The product was worked up as above. A small sample was analyzed by GC as usual which showed this sample had an assay of 99.88 GC area %, which is very close to the above run in which only one dip tube had been employed. This run demonstrated that multiple dip tubes can be used to cut the DPE feed time significantly, without affecting product assay very much.

EXAMPLE 3

A 1-L round bottom flask was equipped exactly as in the above Examples. The flask was charged with bromine (12.5 moles, 1997.5 g, 644.4 mL, 150% stoichiometric excess) and anhydrous aluminum chloride (14 g, 15 wt. % based on the amount of DPE used). The slurry was stirred and heated to 55° C. Prior to this, a 44.9 wt % DPE solution was prepared by dissolving DPE (91.1 g, 0.5 mole) in dibromomethane (45 mL). This solution was now fed to the reactor containing bromine and catalyst at 55° C. as usual, via a $\frac{1}{16}$-inch (ca. 0.16 cm) I.D. Teflon dip tube, sub-surface to bromine, at 55° C. The feed was over in 8 hours. The reaction mixture was now heated and stirred at reflux (63° C.) for an additional 30 minutes. The reaction mixture was now cooled to room temperature and water (300 mL) was added. The equipment was set for steam distillation of bromine and solvent by installing a Barret trap. The reaction mixture and water slurry was now heated and bromine/solvent was removed overhead while continuously recycling the water back to the reactor. After about 175 mL of the bromine/solvent was removed, an additional 200 mL of water was added to replace the volume of bromine/solvent removed overhead. After about a total of 375 mL of solvent and bromine had been removed, the vapor temperature had reached 70° C. and the product started foaming. Since there wasn't enough room in the reactor to handle the froth, distillation was stopped at this point and the slurry cooled and caustic was added. (50% aq. NaOH, 65 g). The product was filtered and washed with water (5×250 mL) and allowed to dry in air overnight to give 458.7 g. of an orange solid. A GC analysis was performed which gave an assay for this product of 100 GC area % (as compared with the expected 99.95 GC area %). This run demonstrates that increased level of catalyst also improves the assay of decabromodiphenylethane to some degree.

EXAMPLE 4

This run was an exact repeat of Example 3 except that two dip tubes were employed to feed the solution. The feed time was, therefore, reduced to 4 hours. The work-up was as usual. The air-dried product weighed 472.64 g. A sample analyzed by GC showed the assay to be 99.74 GC area % of decabromodiphenylethane. After heating at 220° C. for 4 hours, the sample showed the assay to be 99.77 GC area %. Again, this run demonstrates that product of similar assay is obtained by using multiple diptubes as in the case of corresponding single dip tube process, with the advantage of being able to significantly reduce the DPE feed time.

The importance of avoiding overlap or intersection of two or more flows of DPE into the reaction mixture was shown by a pair of experiments conducted in a manner similar to the procedures given in the above examples. In one experiment, one dip tube was used whereas in another, two dip tubes were used but they were too close together for the feed rate used, so that the feeds overlapped each other before completion of bromination. In Run A in which one dip tube was used, the DPE feed rate was 0.3 g/min whereas in Run B in which two dip tubes with overlapping feeds were used, the DPE feed rate was 0.6 g/min. The decabromodiphenylethane product formed in Run A had an assay by GC of 91.20 area percent. The product formed in Run B had an assay by GC of only 87.08 area percent.

As noted above and as used herein including the claims:
1) The term "reaction-derived" means that the composition of the product is reaction determined and not the result of use of downstream purification techniques, such as recrystallization or chromatography, or like procedures that can affect the chemical composition of the product. Adding water or an aqueous base such as sodium hydroxide to the reaction mixture to inactivate the catalyst, and washing away of non-chemically bound impurities by use of aqueous washes such as with water or dilute aqueous bases are not excluded by the term "reaction-derived". In other words, the products are directly produced in the synthesis process without use of any subsequent procedure to remove or that removes nonabromodiphenyl ethane from decabromodiphenyl ethane.
2) Unless expressly stated otherwise, the term "high assay" means that the reaction-derived decabromodiphenylethane product comprises at least about 99.50 GC area % of decabromodiphenylethane with the balance consisting essentially of nonabromodiphenylethane.

Typically, the nonabromodiphenylethane is in the form of at least one isomer of nonabromodiphenylethane and preferably is in the form of at least two isomers of nonabromodiphenylethane in an amount not exceeding about 0.50 GC area percent, preferably not exceeding about 0.30 GC area percent, and still more preferably, not exceeding about 0.10 GC area percent. Especially preferred high assay reaction-derived decabromodiphenylethane products of this invention contain no detectable amount by the GC procedure of octabromodiphenylethane or any other polybromodiphenylethane having less than 9 bromine atoms per molecule.

The high assay reaction-derived decabromodiphenylethane products formed in processes of this invention are white or slightly off-white in color. White color is advantageous as it simplifies the end-users task of insuring consistency of color in the articles that are flame retarded with such products.

The decabromodiphenylethane products formed in the processes of this invention may be used as flame retardants in formulations with virtually any flammable material. The material may be macromolecular, for example, a cellulosic material or a polymer. Illustrative polymers are: olefin polymers, cross-linked and otherwise, for example homopolymers of ethylene, propylene, and butylene; copolymers of two or more of such alkene monomers and copolymers of one or more of such alkene monomers and other copolymerizable monomers, for example, ethylene/propylene copolymers, ethylene/ethyl acrylate copolymers and ethylene/propylene copolymers, ethylene/acrylate copolymers and ethylene/vinyl acetate copolymers; polymers of olefinically unsaturated monomers, for example, polystyrene, e.g. high impact polystyrene, and styrene copolymers, polyurethanes; polyamides; polyimides; polycarbonates; polyethers; acrylic resins; polyesters, especially poly(ethyleneterephthalate) and poly(butyleneterephthalate); polyvinyl chloride; thermosets, for example, epoxy resins; elastomers, for example, butadiene/styrene copolymers and butadiene/acrylonitrile copolymers; terpolymers of acrylonitrile, butadiene and styrene; natural rubber; butyl rubber and polysiloxanes. The polymer may be, where appropriate, cross-linked by chemical means or by irradiation. The decabromodiphenylethane products formed in a process of this invention can also be used in textile applications, such as in latex-based back coatings.

The amount of a high assay reaction-derived decabromodiphenylethane product formed pursuant to this invention (hereinafter Product of the invention) used in a formulation will be that quantity needed to obtain the flame retardancy sought. In general, the formulation and resultant product may contain from about 1 to about 30 wt %, preferably from about 5 to about 25 wt % of Product of the invention. Master batches of polymer containing decabromodiphenylethane, which are blended with additional amounts of substrate polymer, typically contain even higher concentrations of decabromodiphenylethane, e.g., up to 50 wt % or more.

It is advantageous to use the Product of the invention in combination with antimony-based synergists, e.g. $Sb_2O_3$. Such use is conventionally practiced in all decabromodiphenylethane applications. Generally, the Product of the invention will be used with the antimony based synergists in a weight ratio ranging from about 1:1 to 7:1, and preferably of from about 2:1 to about 4:1.

Any of several conventional additives used in thermoplastic formulations may be used, in their respective conventional amounts, with Product of the invention, e.g., plasticizers, antioxidants, fillers, pigments, UV stabilizers, etc.

Thermoplastic articles formed from formulations containing a thermoplastic polymer and Product of the invention can be produced conventionally, e.g., by injection molding, extrusion molding, compression molding, and the like. Blow molding may also be appropriate in certain cases.

Components referred to by chemical name or formula anywhere in the specification or claims hereof, whether referred to in the singular or plural, are identified as they exist prior to coming into contact with another substance referred to by chemical name or chemical type (e.g., another component, a solvent, or etc.). It matters not what chemical changes, transformations and/or reactions, if any, take place in the resulting mixture or solution as such changes, transformations, and/or reactions are the natural result of bringing the specified components together under the conditions called for pursuant to this disclosure. Thus the components are identified as ingredients to be brought together in connection with performing a desired operation or in forming a desired composition. Also, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that a substance, component or ingredient may have lost its original identity through a chemical reaction or transformation during the course of contacting, blending or mixing operations, if conducted in accordance with this disclosure and with ordinary skill of a chemist, is thus of no practical concern.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text expressly indicates otherwise.

Each and every patent or publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove.

The invention claimed is:

1. A reaction-derived decabromodiphenylethane solid comprising (i) at least about 99.50 GC area % of decabromodiphenylethane and (ii) nonabromodiphenyl ethane in an amount not exceeding about 0.50 GC area %.

2. A reaction-derived decabromodiphenylethane solid as in claim 1 comprising (i) at least about 99.50 GC area % of decabromodiphenylethane and (ii) nonabromodiphenyl ethane in an amount not exceeding about 0.30 GC area %.

3. A reaction-derived decabromodiphenylethane solid as in claim 1 comprising (i) at least about 99.50 GC area % of decabromodiphenylethane and (ii) nonabromodiphenyl ethane in an amount not exceeding about 0.10 GC area %.

4. A reaction-derived decabromodiphenylethane solid as in claim 1 comprising (i) at least about 99.80 GC area % of decabromodiphenylethane and (ii) nonabromodiphenyl ethane in an amount not exceeding about 0.20 GC area %.

5. A reaction-derived decabromodiphenylethane solid as in claim 1 comprising (i) at least about 99.90 GC area % of decabromodiphenylethane and (ii) nonabromodiphenyl ethane in an amount not exceeding about 0.10 GC area %.

6. A flammable macromolecular material with which has been blended or included a flame retardant amount of a reaction-derived decabromodiphenylethane solid comprising (i) at least about 99.50 GC area % of decabromodiphenylethane and (ii) nonabromodiphenyl ethane in an amount not exceeding about 0.50 GC area %.

7. The material of claim 6 wherein the macromolecular material is a thermoplastic, a thermoset, or a latex-based back coating.

8. The material of claim 6 wherein the macromolecular material is a thermoplastic polymer.

9. The material of any of claims 6-8 wherein the amount of the nonabromodiphenyl ethane in said reaction-derived decabromodiphenylethane solid prior to blending with or inclusion in said material is an amount that does not exceed about 0.30 GC area %.

10. The material of any of claims 6-8 wherein the amount of the nonabromodiphenyl ethane in said reaction-derived decabromodiphenylethane solid prior to blending with or inclusion in said material is an amount that does not exceed about 0.10 GC area %.

11. The material of any of claims 6-8 wherein said reaction-derived decabromodiphenylethane solid prior to blending with or inclusion in said material comprises (i) at least about 99.80 GC area % of decabromodiphenylethane and (ii) nonabromodiphenyl ethane in an amount not exceeding about 0.20 GC area %.

12. The material of any of claims 6-8 wherein said reaction-derived decabromodiphenylethane solid prior to blending with or inclusion in said material comprises (i) at least about 99.90 GC area % of decabromodiphenylethane and (ii) nonabromodiphenyl ethane in an amount not exceeding about 0.10 GC area %.

* * * * *